United States Patent
Ueno et al.

(10) Patent No.: US 9,974,972 B2
(45) Date of Patent: May 22, 2018

(54) LIGHTING SYSTEM, OPERATION DEVICE, AND LIGHT IRRADIATION METHOD

(71) Applicant: Panasonic Intellectual Property Management Co., Ltd., Osaka (JP)

(72) Inventors: Saori Ueno, Osaka (JP); Yuri Fujiwara, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days. days.

(21) Appl. No.: 15/348,100

(22) Filed: Nov. 10, 2016

(65) Prior Publication Data

US 2017/0136259 A1   May 18, 2017

(30) Foreign Application Priority Data

Nov. 12, 2015  (JP) .................................. 2015-222477

(51) Int. Cl.
| | |
|---|---|
| H05B 37/02 | (2006.01) |
| A61N 5/06 | (2006.01) |
| A61M 21/02 | (2006.01) |
| G06F 3/0481 | (2013.01) |
| A61M 21/00 | (2006.01) |
| G06F 3/0484 | (2013.01) |

(52) U.S. Cl.
CPC ........... *A61N 5/0618* (2013.01); *A61M 21/02* (2013.01); *G06F 3/04817* (2013.01);
(Continued)

(58) Field of Classification Search
CPC ........................ G06F 3/04817; G06F 3/04847; A61M 21/02; A61M 2021/0044;
(Continued)

(56) References Cited

U.S. PATENT DOCUMENTS 7,236,154 B1 *  6/2007  Kerr ...................... G06F 1/1616
                                                       345/102
9,743,491 B2 *  8/2017  Loeb .................. H05B 37/0227
(Continued)

FOREIGN PATENT DOCUMENTS

| JP | 08-193738 | 7/1996 |
|---|---|---|
| JP | 2003-164527 A | 6/2003 |

(Continued)

*Primary Examiner* — Douglas W Owens
*Assistant Examiner* — Amy Yang
(74) *Attorney, Agent, or Firm* — McDermott Will & Emery LLP

(57) ABSTRACT

A lighting system includes: an illumination light source which irradiates a user with illumination light; a user interface which receives a user operation; a controller which controls an amount of light of the illumination light source and an irradiation period of the illumination light source; and a storage which stores characteristic information having a negative correlation between the amount of light and the irradiation period. When the user interface receives a user operation which specifies a value of one of the amount of light and the irradiation period, the controller determines a value of the other according to the characteristic information and controls the illumination light source according to the specified value of the one of the amount of light and the irradiation period and the determined value of the other.

9 Claims, 26 Drawing Sheets

(52) U.S. Cl.
CPC ......... *H05B 37/02* (2013.01); *H05B 37/0281* (2013.01); *A61M 2021/0044* (2013.01); *A61M 2205/505* (2013.01); *A61N 2005/0626* (2013.01); *A61N 2005/0663* (2013.01); *G06F 3/04847* (2013.01); *Y02B 20/42* (2013.01)

(58) Field of Classification Search
CPC .... A61N 2005/0663; A61N 2005/0626; A61N 5/0618; H05B 37/02; H05B 37/0281
USPC .................................................. 315/129, 297
See application file for complete search history.

(56) References Cited

U.S. PATENT DOCUMENTS

| | | | | |
|---|---|---|---|---|
| 2004/0249423 | A1* | 12/2004 | Savage | A61M 21/00 607/88 |
| 2013/0172963 | A1* | 7/2013 | Moffat | A61N 5/0616 607/94 |
| 2013/0238060 | A1* | 9/2013 | Nevins | A61N 5/0613 607/90 |
| 2013/0328503 | A1 | 12/2013 | Toda | |
| 2015/0062892 | A1* | 3/2015 | Krames | H05B 37/0281 362/231 |
| 2016/0366746 | A1* | 12/2016 | van de Ven | F21V 29/74 |
| 2017/0238401 | A1* | 8/2017 | Sadwick | H05B 37/0281 315/294 |

FOREIGN PATENT DOCUMENTS

| | | |
|---|---|---|
| JP | 2003-223994 A | 8/2003 |
| JP | 2008-084678 A | 4/2008 |
| JP | 2013-254669 A | 12/2013 |
| JP | 2014-013276 | 1/2014 |
| JP | 2014-044915 A | 3/2014 |
| JP | 2014-183014 | 9/2014 |

* cited by examiner

FIG. 10

| MENSTRUATION-RELATED INFORMATION | 21b |
|---|---|
| NUMBER OF DAYS OF MENSTRUAL CYCLE | d1 |
| DATE OF MENSTRUATION ONSET | d2 |
| MENSTRUAL CYCLE | d3 |
| BASAL BODY TEMPERATURE | d4 |
| AMOUNT OF LUTEINIZING HORMONE SECRETION | d5 |
| AMOUNT OF LUTEOHORMONE SECRETION | d6 |
| AMOUNT OF ESTROGENIC HORMONE SECRETION | d7 |
| SUBJECTIVE LEVEL OF MENSTRUAL PAIN | d8 |
| EACH ITEM OF SUBJECTIVE ESTIMATION OF PREMENSTRUAL SYNDROME PPST | d9 |
| EACH ITEM OF SUBJECTIVE ESTIMATION OF PREMENSTRUAL SYNDROME PSQ | d10 |

FIG. 11A

| PSST <MENTAL AND PHYSICAL SYMPTOMS> | |
|---|---|
| 1. ANGER / IRRITABILITY | a/b/c/d |
| 2. ANXIETY / TENSION | a/b/c/d |
| 3. TEARFUL / EMOTIONAL DISTURBANCE | a/b/c/d |
| 4. DEPRESSED MOOD / LIKELY TO BE DEPRESSED | a/b/c/d |
| 5. DECREASED INTEREST IN STUDY OR WORK ACTIVITIES | a/b/c/d |
| 6. NOT BEING ABLE TO DO HOUSEWORK / DECREASED INTEREST IN HOME ACTIVITIES | a/b/c/d |
| 7. DECREASED INTEREST IN DAILY OR SOCIAL ACTIVITIES | a/b/c/d |
| 8. DIFFICULTY IN CONCENTRATING | a/b/c/d |
| 9. FATIGUE / LACK OF ENERGY | a/b/c/d |
| 10. INCREASED FOOD CRAVINGS | a/b/c/d |
| 11. INSOMNIA | a/b/c/d |
| 12. HYPERSOMNIA | a/b/c/d |
| 13. UNCONTROLLABLE EMOTION | a/b/c/d |
| 14-1. BREAST TENDERNESS / PAIN | a/b/c/d |
| 14-2. HEADACHES | a/b/c/d |
| 14-3. MUSCLE / JOINT PAIN | a/b/c/d |
| 14-4. BLOATING | a/b/c/d |
| 14-5. SWELLING / WEIGHT GAIN | a/b/c/d | a NO
b YES BUT DO NOT MIND
c BARELY TOLERABLE
d POSING PROBLEM FOR DAILY LIFE

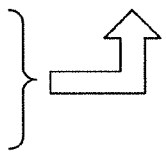

FIG. 12

PSQ

| (A) DO THE FOLLOWING SYMPTOMS APPEAR ONE TO TWO WEEKS BEFORE MENSTRUAL ONSET? | |
|---|---|
| 1 FEEL SAD, DEPRESSED, BLUE, HOPELESS, WORTHLESS, OR GUILTY | i/j/k/l |
| 2 FEEL ANXIOUS, TENSE, AGITATED, OR IRRITATED | i/j/k/l |
| 3 SUDDENLY FEEL SAD OR TEARFUL, SENSITIVE TO REJECTION, OR FEELINGS ARE EASILY HURT | i/j/k/l |
| 4 FEEL ANGRY OR IRRITABLE | i/j/k/l |
| 5 HAVE LESS INTEREST IN USUAL ACTIVITIES (FRIENDS, HOBBIES, SCHOOL) | i/j/k/l |
| 6 HAVE DIFFICULTY IN CONCENTRATING | i/j/k/l |
| 7 FEEL LETHARGIC, TIRED, OR FATIGUED | i/j/k/l |
| 8 FEEL HUNGRY ALL THE TIME AND OVEREAT, OR HAVE CRAVINGS FOR SPECIFIC FOOD | i/j/k/l |
| 9 SLEEP TOO MUCH, FIND IT HARD TO GET UP, HAVE TROUBLE GETTING TO SLEEP OR STAYING ASLEEP | i/j/k/l |
| 10 FEEL OVERWHELMED OR UNABLE TO COPE, OR FEEL OUT OF CONTROL | i/j/k/l |
| 11 FEEL BREAST SWELLING OR TENDERNESS, HAVE HEADACHE, JOINT OR MUSCLE PAIN, GAIN WEIGHT, OR FEEL BLOATED SENSATION | i/j/k/l |
| (B) AT LEAST ONE OF THE ABOVE 1 TO 11 UNPLEASANT SYMPTOMS CAUSE THE FOLLOWINGS? | |
| 1 REDUCTION IN EFFICIENCY OR PRODUCTIVITY IN WORK, STUDY, OR HOUSEWORK IN DAILY ROUTINE AT WORK, SCHOOL, OR HOME | i/j/k/l |
| 2 QUITTING OF OR LESS PARTICIPATION IN HOBBIES, CLUB ACTIVITIES, OR SOCIAL ACTIVITIES | i/j/k/l |
| 3 POSING PROBLEM FOR RELATIONSHIPS WITH OTHERS | i/j/k/l | i NOT AT ALL
j MILD
k MODERATE
l SEVERE

FIG. 13

| DAYS AFTER MENSTRUATION ONSET | PHASE | PERIOD OF DEVELOPING PMS | MENTAL STATE | PHYSICAL STATE | SKIN CONDITIONS |
|---|---|---|---|---|---|
| 1-7 | ANTERIOR HALF OF MENSTRUAL PHASE | ←———→ | IRRITABILITY, DEPRESSION, LACK OF MENTAL STABILITY, EMOTIONAL SENSITIVITY | BREAST TENDERNESS, FATIGUE, BODY WEIGHT GAIN, SWELLING, HEADACHE, ABDOMINAL BLOATING SENSATION, ABDOMINAL CRAMPS, LOWER BACK PAIN, CONSTIPATION, DROWSINESS, FOOD CRAVINGS | EXCESSIVE SEBACEOUS SECRETION, LIKELY TO GET PIMPLES OR ACNES |
| | LATTER HALF OF MENSTRUAL PHASE | | EMOTIONALLY UPBEAT, MENTALLY VIGOROUS | ANEMIA, HEADACHE, COLD BODY, POOR BLOOD CIRCULATION, MENSTRUAL CRAMPS, LOWERED RESISTANCE | SENSITIVE SKIN, DRY SKIN |
| 8-14 | FOLLICULAR PHASE | | SOCIABLE, CHEERFUL, POSITIVE THINKING | REFRESHED, EASY TO DIET | GOOD CONDITION, SUITABLE FOR SKIN CARE |
| 15-21 | OVULATION PHASE ANTERIOR HALF OF LUTEAL PHASE | | FREQUENT MOOD SWINGS | DISCOMFORT/UNCOMFORTABLE FEELING IN ABDOMEN, SWELLING, CONSTIPATION, STIFF SHOULDER, LOWER BACK PAIN, DIFFICULT TO DIET | RELATIVELY GOOD CONDITION, RELATIVELY SUITABLE FOR SKIN CARE |
| 22-28 | LATTER HALF OF LUTEAL PHASE | ←———→ | IRRITABILITY, DEPRESSION, LACK OF MENTAL STABILITY, EMOTIONAL SENSITIVITY | BREAST TENDERNESS, FATIGUE, BODY WEIGHT GAIN, SWELLING, HEADACHE, ABDOMINAL BLOATING SENSATION, ABDOMINAL CRAMPS, LOWER BACK PAIN, CONSTIPATION, DROWSINESS, FOOD CRAVINGS | EXCESSIVE SEBACEOUS SECRETION, LIKELY TO GET PIMPLES, ACNES, SKIN BLEMISHES, OR FRECKLES |

FIG. 18

| SLEEP-RELATED INFORMATION | 21c |
|---|---|
| SLEEP LENGTH OF PREVIOUS DAY | d21 |
| TIME OF SLEEP | d22 |
| AWAKING TIME OF THE DAY | d23 |
| SLEEP LENGTH OF SEVERAL DAYS | d24 |
| AMOUNT OF ACTIVITY | d25 |
| SUBJECTIVE ESTIMATION OF SLEEP QUALITY | d26 |
| SUBJECTIVE SATISFACTION LEVEL OF SLEEP | d27 |

FIG. 19

SUBJECTIVE ESTIMATION OF SLEEP QUALITY

1. I STILL FEEL TIRED |—|—|—|—| I DO NOT FEEL TIRED
2. I HAVE POWER OF CONCENTRATION |—|—|—|—| I HAVE NO POWER OF CONCENTRATION
3. I SLEPT SOUNDLY |—|—|—|—| I DID NOT SLEEP WELL
4. I FEEL SENSE OF RELEASE |—|—|—|—| I FEEL STRESSED
5. I FEEL LANGUID |—|—|—|—| I FEEL PHYSICALLY BRACED UP
6. I HAVE GOOD APPETITE |—|—|—|—| I HAVE NO APPETITE
7. I WAS IN LONG STUPOR STATE BOFORE SLEEP |—|—|—|—| I WAS IN LESS STUPOR STATE BOFORE SLEEP
8. MY HEAD IS CLEAR |—|—|—|—| MY HEAD IS STUFFY
9. I HAD LOTS OF NIGHTMARE |—|—|—|—| I HAD NO NIGHTMARE
10. I FELL ASLEEP EASILY |—|—|—|—| I HAD TROUBLE GETTING TO SLEEP
11. I FEEL UNPLEASANT |—|—|—|—| I FEEL REFRESHED
12. I HAD LOTS OF DREAMS |—|—|—|—| I HAD NO DREAM
13. I AWOKE A LOT DURING SLEEP |—|—|—|—| I DID NOT AWAKE DURING SLEEP
14. I CAN ANSWER THIS SURVEY RIGHT AWAY |—|—|—|—| I FEEL RELUCTANT TO ANSWER THIS SURVEY
15. I HAD LONG SLEEP |—|—|—|—| I HAD SHORT SLEEP
16. I HAD SHALLOW SLEEP |—|—|—|—| I HAD DEEP SLEEP a: VERY MUCH (TRUE OF LEFT ITEM)
b: SLIGHTLY (TRUE OF LEFT ITEM)
c: SLIGHTLY (TRUE OF RIGHT ITEM)
d: VERY MUCH (TRUE OF RIGHT ITEM)

LIGHTING SYSTEM, OPERATION DEVICE, AND LIGHT IRRADIATION METHOD

CROSS REFERENCE TO RELATED APPLICATION

This application claims the benefit of priority of Japanese Patent Application Number 2015-222477 filed on Nov. 12, 2015, the entire content of which is hereby incorporated by reference.

BACKGROUND

1. Technical Field

The present disclosure relates to a lighting system, an operation device, and a light irradiation method, for irradiating a user with illumination light.

2. Description of the Related Art

It is generally known that premenstrual syndrome (PMS) or a sleep disorder is alleviated by exposing a biological body to a suitable amount of light.

Japanese Unexamined Patent Application Publication No. 2003-164527 discloses a sleeping environmental controller for woman which includes: a physical condition judging unit for judging the present physical condition; a temperature control unit for controlling a temperature in the bed environment, and a control unit for controlling the operation of the temperature control unit on the basis of the judged present physical condition.

SUMMARY

However, although a suitable combination of an amount of light and an irradiation period is scientifically verified, it is difficult for a user who is not an expert to configure the combination into a lighting system. In other word, even when a user have requests regarding an amount of light or an irradiation period (for example, hoping to be exposed to weak light or strong light, hoping to shorten the irradiation period or lengthen the irradiation period), it is difficult to specify a suitable combination of an amount of light and an irradiation period.

The present disclosure provides a lighting system, an operation device, and a light irradiation method, which facilitate user's specifying of a desired amount of light or an irradiation period.

In order to achieve the above-described object, a lighting system according to an aspect of the present disclosure is a lighting system, including: an illumination light source which irradiates a user with illumination light; a user interface which receives a user operation; a controller which controls an amount of light of the illumination light source and an irradiation period of the illumination light source; and a storage which stores characteristic information having a negative correlation between the amount of light of the illumination light source and the irradiation period, wherein when the user interface receives a user operation which specifies a value of one of the amount of light of the illumination light source and the irradiation period, the controller determines a value of the other of the amount of light of the illumination light source and the irradiation period according to the characteristic information and controls the illumination light source according to the value of the one of the amount of light of the illumination light source and the irradiation period which has been specified and the value of the other of the amount of light of the illumination light source and the irradiation period which has been determined.

In addition, an operation device according to an aspect of the present disclosure is an which controls an illumination light source that irradiates a user with illumination light, the operation device including: user interface which receives a user operation; a controller which controls an amount of light of the illumination light source and an irradiation period of the illumination light source; and a storage which stores characteristic information having a negative correlation between the amount of light of the illumination light source and the irradiation period, wherein when the user interface receives an operation which specifies a value of one of the amount of light of the illumination light source and the irradiation period, the controller determines a value of the other of the amount of light of the illumination light source and the irradiation period according to the characteristic information and controls the illumination light source according to the value of the one of the amount of light of the illumination light source and the irradiation period which has been specified and the value of the other of the amount of light of the illumination light source and the irradiation period which has been determined.

A light irradiation method according to an aspect of the present disclosure is a light irradiation method for irradiating a user with illumination light, the light irradiation method including: receiving a user operation which specifies a value of one of an amount of light and, an irradiation period; determining a value of the other of the amount of light and the irradiation period which is not specified, according to characteristic information having a negative correlation between the amount of light and the irradiation period; and irradiating the user with the illumination light according to the value of the one of the amount of light and the irradiation period which has been specified and the value of the other of the amount of light and the irradiation period which has been determined.

With the lighting system, the operation device, and the light irradiation method, according to the present disclosure, it is possible to facilitate user's specifying of a desired amount of light or an irradiation period. More specifically, a user can specify an amount of light or an irradiation period without taking time and labor, and be irradiated with light with a suitable combination of an amount of light and an irradiation period.

BRIEF DESCRIPTION OF DRAWINGS

The figures depict one or more implementations in accordance with the present teaching, by way of examples only, not by way of limitations, in the figures, like reference numerals refer to the same or similar elements.

FIG. 10 is an explanatory diagram illustrating an example of menstruation-related information according to Embodiment 2;

FIG. 11A is a diagram illustrating an example of data items related to mental and physical symptoms of the PSST illustrated in FIG. 10;

FIG. 12 is an explanatory diagram illustrating an example of data items related to the PSQ illustrated in FIG. 10;

FIG. 13 is a diagram illustrating mental, physical, and skin conditions according to a menstrual cycle;

FIG. 18 is an explanatory diagram illustrating an example of data items of sleep-related information according to the modification exampled of Embodiment 2;

FIG. 19 is an explanatory diagram illustrating an example of data items of part of sleep-related information according o the modification example of Embodiment 2;

DETAILED DESCRIPTION OF THE EMBODIMENTS

The following describes in detail embodiments according to the present disclosure, with reference to the drawings. It should be noted that each of the embodiments explained below describes a specific example of the present disclosure. The numerical values, shapes, materials, structural components, the disposition and connection of the structural components, steps, the processing order of the steps, etc. described in the following embodiments are mere examples, and do not intend to limit the present disclosure. Furthermore, among the structural components in the following embodiments, structural components not recited in any one of the independent claims which indicate the broadest concepts of the present disclosure are described as arbitrary structural components. Moreover, each diagram is a schematic diagram and not necessarily strictly illustrated.

(Embodiment 1)

[1.1 A Configuration Example of a Lighting System]

First, the following describes a configuration of a lighting system according to Embodiment 1. The lighting system according to the present embodiment is used for, for example, optical treatment for improving premenstrual syndrome (PMS), a sleep disorder, depression, etc.

Figure 1:
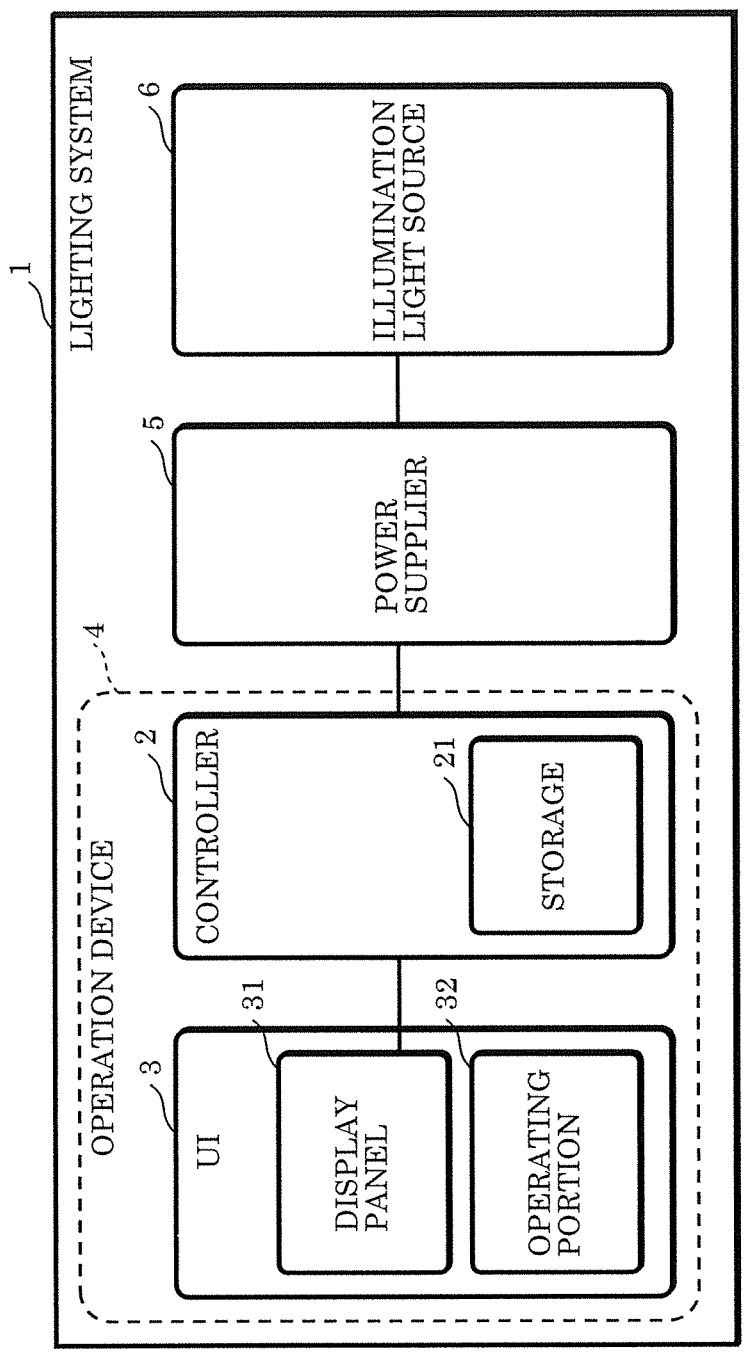
FIG. 1 is a block diagram illustrating a configuration example of a lighting system according to Embodiment 1.

FIG. 1 is a block diagram illustrating a configuration example of lighting system 1 according to Embodiment 1. Lighting system 1 illustrated in the diagram includes illumination light source 6, power supplier 5, and operation device 4.

Illumination light source 6 irradiates a user with illumination light. The illumination light may be white light, for example, and is radiated to part or all of user's body while the user sits on a chair or lies on a bed. Illumination light source 6 may have a toning function in addition to a dimming function. The dimming function and the toning function may be controlled by operation device 4 via power supplier 5.

Power supplier 5 supplies power to illumination light source 6.

Operation device 4 includes controller 2 and user interface (hereinafter abbreviated as UI) 3, and receives a user operation.

Controller 2 includes storage 21 and controls an amount of light and an irradiation period of illumination light source 6. For example, controller 2 is configured in the form of hardware including a CPU (or a processor), a ROM, and a RAM. The CPU controls the amount of light and the irradiation period of illumination light source 6, by executing a program stored in the ROM or RAM.

Storage 21 stores characteristic information having a negative correlation between the amount of light and the irradiation period. For example, storage 21 is configured in the form of the above-described ROM and RAM.

UI 3 includes display panel 31 and operating portion 32. UI 3 may be, for example, a graphical user interface (GUI) which includes a touch panel as operating portion 32 on a screen of a liquid-crystal display panel as display panel 31.

When UI 3 receives a user operation which specifies a value of one of the amount of light and the irradiation period, controller 2 determines a value of the other according to the characteristic information and controls the illumination light source according to the specified value of the one of the amount of light and the irradiation period and the determined value of the other.

[1.2 A Display Example of the User Interface]

Next, a display example of user interface 3 which receives a user operation shall be described.

Figure 2:
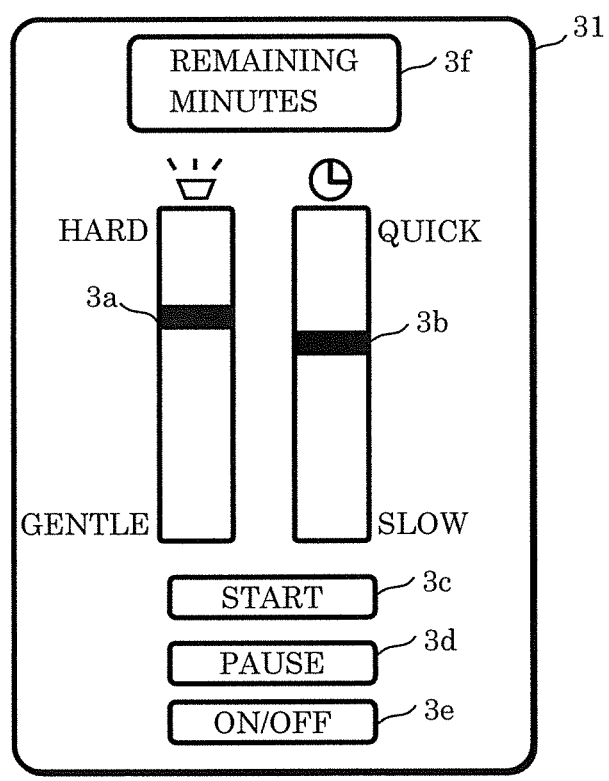
FIG. 2 is a block diagram illustrating a display example of a UI according to Embodiment 1.

FIG. 2 is a diagram illustrating a display example of UI 3 according to Embodiment 1. This diagram illustrates an example of the GUI of display panel 31 included in UI 3. Display item 3a is displayed on display panel 31 in the diagram.

Display item 3a is an operation icon for specifying the amount of light of illumination light source 6, and indicated by a slider icon which can be slid by a user operation within a range from "hard" (the amount of light is great, or illuminance is high) to "gentle" (the amount of light is small, or illuminance is low) illustrated in the diagram. A user can specify a desired amount of light by performing a sliding operation on display item 3a.

Display item 3b is an operation icon for specifying an irradiation period of illumination light source, 6, and indicated by a slider icon which can be slid by a user operation within a range from "quick" (the irradiation period is short) to "slow" (the irradiation period is long) illustrated in the diagram. A user can specify a desired irradiation period by performing a sliding operation on display item 3b.

Display item 3c is an operation icon for instructing start of radiation of illumination light from illumination light source 6 to the user, after the end of the user operation performed on display item 3a or 3b, and indicated by a push button icon.

Display item 3d is an operation icon for instructing pause and restarting of radiation of illumination light from illumination light source 6 to the user, and indicated by a push button icon.

Display item 3e is an operation icon for instructing powering on and off of lighting system 1, or turning on and off of illumination light source 6, and indicated by a push button icon.

Display item 3f is an operation icon for displaying remaining time resulting from subtracting elapsed time of irradiation from the irradiation period specified or set, after radiation of illumination light is started, and indicated by a push button icon.

[1.3 An Example of Characteristic Information]

Next, a specific example of characteristic information shall be described.

Figure 3:
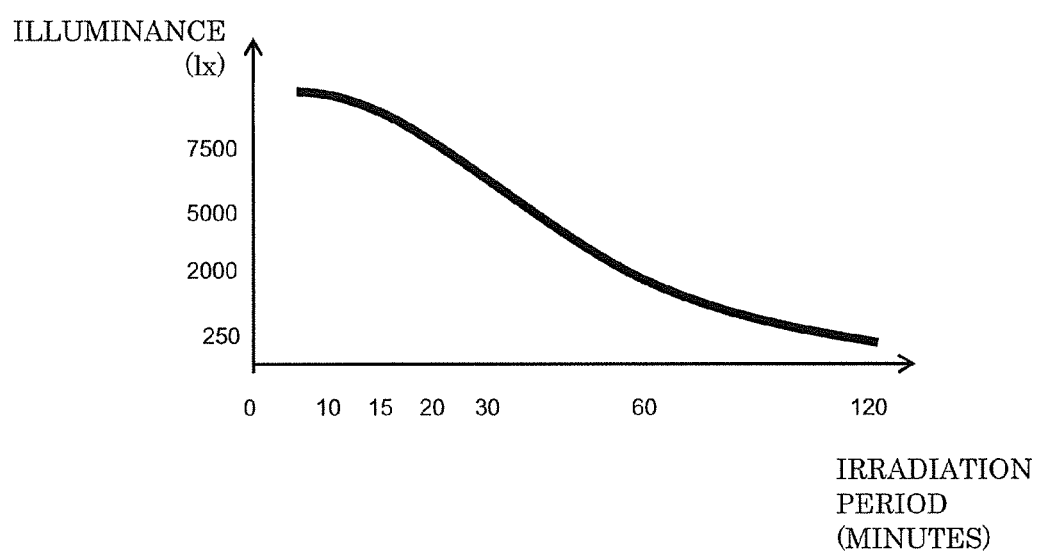
FIG. 3 is a diagram illustrating an example of characteristic information stored in a storage according to Embodiment 1.

FIG. 3 is s diagram illustrating an example of characteristic information stored in storage 21 according to Embodiment 1. The horizontal axis indicates irradiation period (minutes) of illumination light source 6. The vertical axis indicates illuminance (lx) of illumination light emitted from illumination light source 6 to a user. The characteristic information indicates a combination of an amount of light and an irradiation period, which is suitable for improving PMS, depression, a sleep disorder, and has a negative correlation between the amount of light (illuminance) and the irradiation period. The suitable combination between the amount of light and the irradiation period is a combination of an amount of light which a user should be exposed to and an irradiation period, during daytime in a unit period. The unit period is, for example, one day. The time zone in which a user should be exposed to light may be, for example, a time zone in a morning, or may be in a morning or afternoon as long as the time zone is not in time for sleep.

The following describes operations of lighting system 1 configured as described above.

[1.4 An Operation of the Lighting System]

Next, an outline of an operation of lighting system shall be described.

Figure 4:
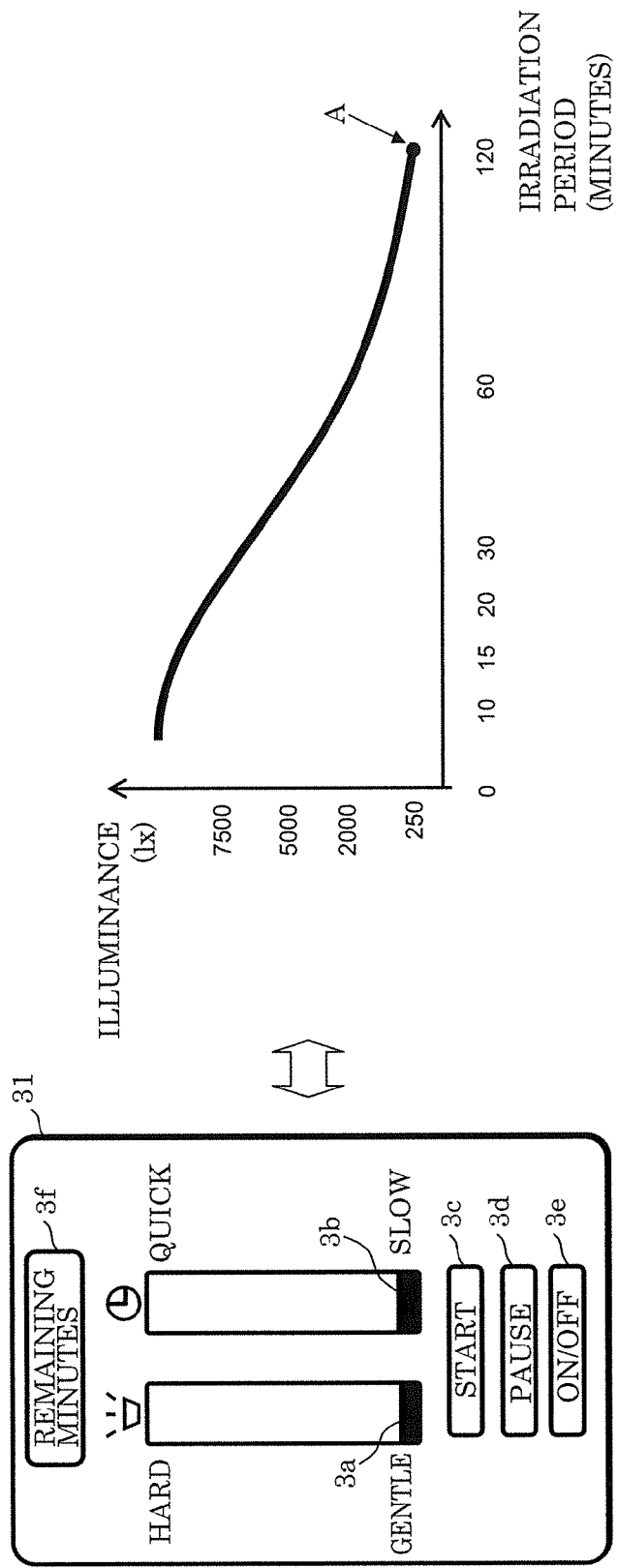
FIG. 4 is an explanatory diagram illustrating a display example of the UI and the characteristic information according to Embodiment 1.
Figure 5:
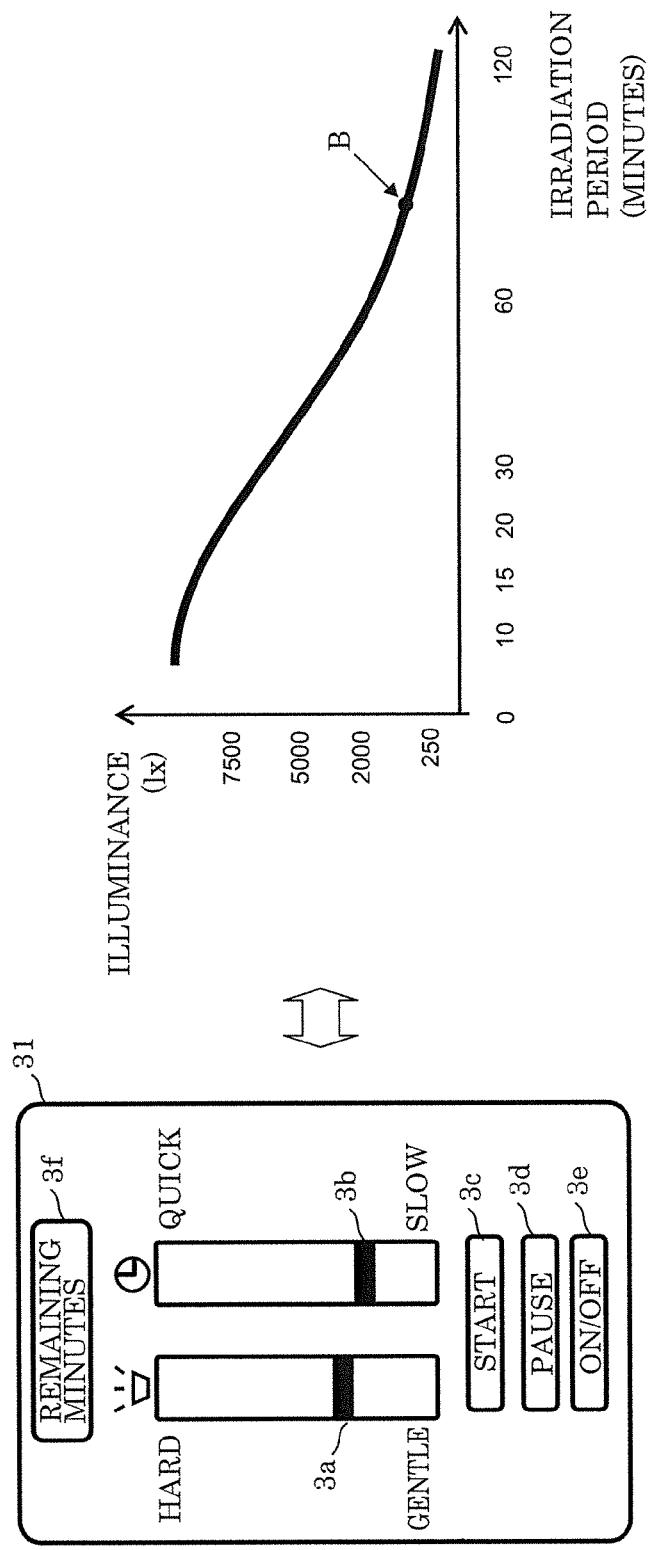
FIG. 5 is an explanatory diagram illustrating a display example of the UI and the characteristic information according to Embodiment 1.

FIG. 4 and FIG. 5 are explanatory diagrams each illustrating a display example of UI 1 and characteristic information according to Embodiment 1.

In the display example illustrated on the left side in FIG. 4, display item 3a indicating the amount of light indicates "gentle" (i.e., the smallest amount of light). In addition, display item 3b indicating the irradiation period indicates "slow" (i.e., longest period). This display example corresponds to point A in the characteristic information illustrated on the right side in FIG. 4, and corresponds to the amount of light (illuminance) of 250 lx and the irradiation period of 120 minutes. With this specifying, the user will be irradiated with the smallest amount of light for 120 minutes. When the user wants to shorten the irradiation period of 120 minutes, it is possible to change the specified irradiation period by performing a user operation on display item 3b.

The display example illustrated on the left side in FIG. 5 shows an example in which the specified irradiation period is changed from the state illustrated on the on the left side in FIG. 4, by a user operation performed on display item 3b. When this change is carried out, controller 2 detects that 90 minutes as the irradiation period has been specified by a user operation performed on display item 3b, and determines the illuminance (the amount of light) corresponding to the irradiation period of 90 minutes by referring to the characteristic information in storage 21. As indicated by point B on the right side in FIG. 5, the illuminance corresponding to the irradiation period of 90 minutes is approximately 500 lx. Accordingly, controller 2 updates the display of display panel 31 to change the sliding position of display item 3a which is not operated by the user, to a position corresponding to the illuminance of 500 lx. With this, display panel 31 shows the display example illustrated on the left side in FIG. 5.

In addition, when the user performs an operation of changing the specified item of display item 3a in the state illustrated on the left side in FIG. 4, controller 2 detects that approximately 500 lx has been specified by a user operation performed on display item 3a, and determines the irradiation period corresponding to the illuminance of 500 lx by referring to the characteristic information in storage 21. As indicated by point B on the right side in FIG. 5, the irradiation period corresponding to the illuminance of approximately 500 lx is approximately 90 minutes. Accordingly, controller 2 updates the display of display panel 31 to change the sliding position of display item 3b which is not operated by the user, to a position corresponding to the irradiation period of 90 minutes. With this updating, display panel 31 shows the display example illustrated on the left, side in FIG. 5.

When a user operation of pressing a start button of display item 3c is carried out in the state illustrated on the left side in FIG. 5, controller 2 causes illumination light source 6 to start emitting illumination light according to a value determined on the basis of the value specified by the user and the value determined from the characteristic information.

[1.5 An Operation Example of Controller 2]

Next, an operation example of lighting system 1 controlled by controller 2 shall be described.

Figure 6:
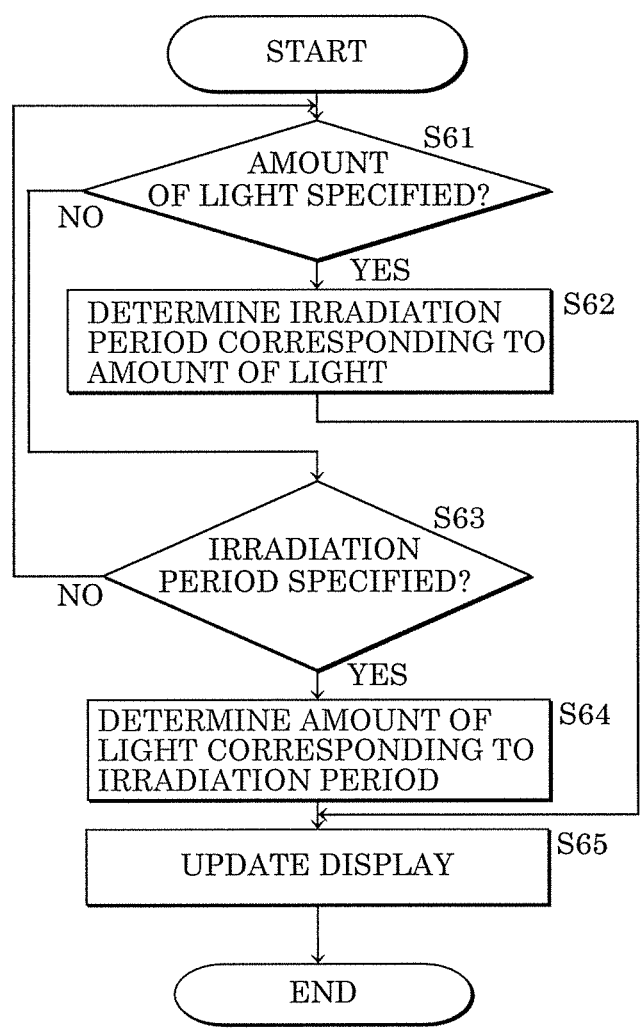
FIG. 6 is a flowchart illustrating an operation example of a controller according to Embodiment 1.

FIG. 6 is a flowchart illustrating an operation example of controller 2 according to Embodiment 1. As described in the diagram, when a user operation of specifying the amount of light is performed on display item 3a of i 3 (S61), controller 2 determines the irradiation period according to the characteristic information (S62). Controller 2 updates display panel 31 to change the slider position of display item 3b which is not operated by the user, to a position corresponding to the determined value (S65).

In addition, when a user operation of specifying the irradiation period is performed on display item 3b of UI 3 (S63), controller 2 determines the amount of light according to the characteristic information (S64). Controller 2 updates display panel 31 to change the slider position of display item 3a which is not operated by the user, to a position corresponding to the determined value (S65).

The operation illustrated by the flowchart of FIG. 6 is executed every time the user operation is performed on display item 3a or 3b.

In this manner, when UI 3 receives a user operation which specifies a value of one of the amount of light and the irradiation period, controller 2 determines a value of the other according to the characteristic information and controls illumination light source 6 according to the specified value of the one of the amount of light and the irradiation period and the determined value of the other.

As described above, with lighting system 1 according to the present embodiment, it is possible to facilitate user's specifying of a desired amount of light or an irradiation period.

As describe above, with the lighting system according to Embodiment 1, it is possible for a user to specify with no inhibition desired one of parameters (one of the amount of light and the irradiation period) without the need to consider a suitable combination of the amount of light and the irradiation period in optical treatment. In other words, a user can obtain a suitable combination of the amount of light and the irradiation period in lighting system 1, by specifying a request regarding the amount of light or the irradiation period (for example, hoping to be exposed to weak light or strong light, hoping to shorten the irradiation period or lengthen the irradiation period).

In addition, a user can easily specify a desired parameter while visually observing display items of parameters (here, the amount of light or the irradiation period).

(Embodiment 2)

Embodiment 2 describes a configuration in which storage 21 stores, as the characteristic information, a plurality of characteristic curve data items having mutually different negative correlations.

[2.1 A Configuration Example of a Lighting System]

First, the following describes a configuration of a lighting system according to Embodiment 2.

A configuration example of lighting system 1 according to Embodiment 2 may be substantially the same as the configuration example illustrated in FIG. 1, and thus the following description focuses on different points.

Figure 7:
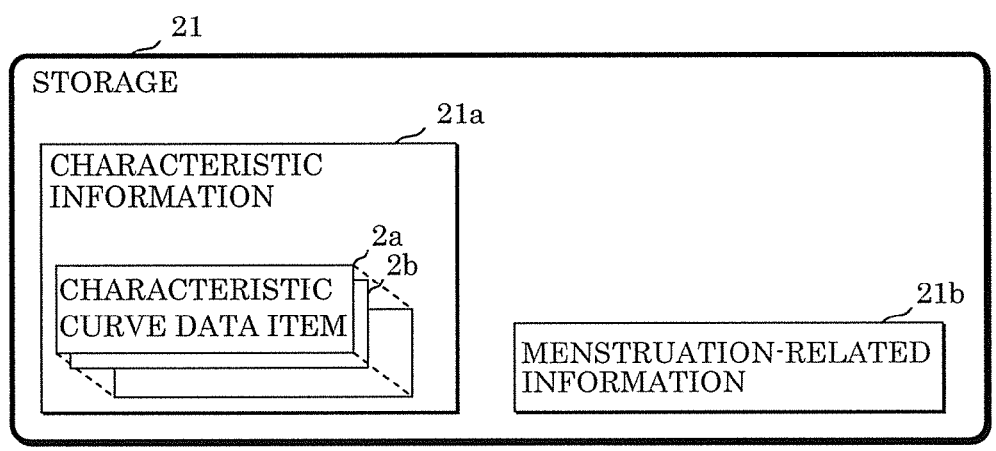
FIG. 7 is an explanatory diagram illustrating an example of characteristic information and menstruation-related information stored in a storage according to Embodiment 2.

FIG. 7 is an explanatory diagram illustrating an example of characteristic information and menstruation-related information stored in storage 21 according to Embodiment 2.

Storage 21 stores characteristic information 21a and menstruation-related information 21b. Characteristic information 21a includes a plurality of characteristic curve data items 2a, 2b, . . . having mutually different negative correlations. Menstruation-related information 21b indicates, for example, severity of symptoms of the premenstrual syndrome of a user, and is a reference for selecting one of the plurality of characteristic curve data items.

[2.2 A Display Example of the User Interface]

Next, a display example of user interface 3 which receives a user operation shall be described.

Figure 8:
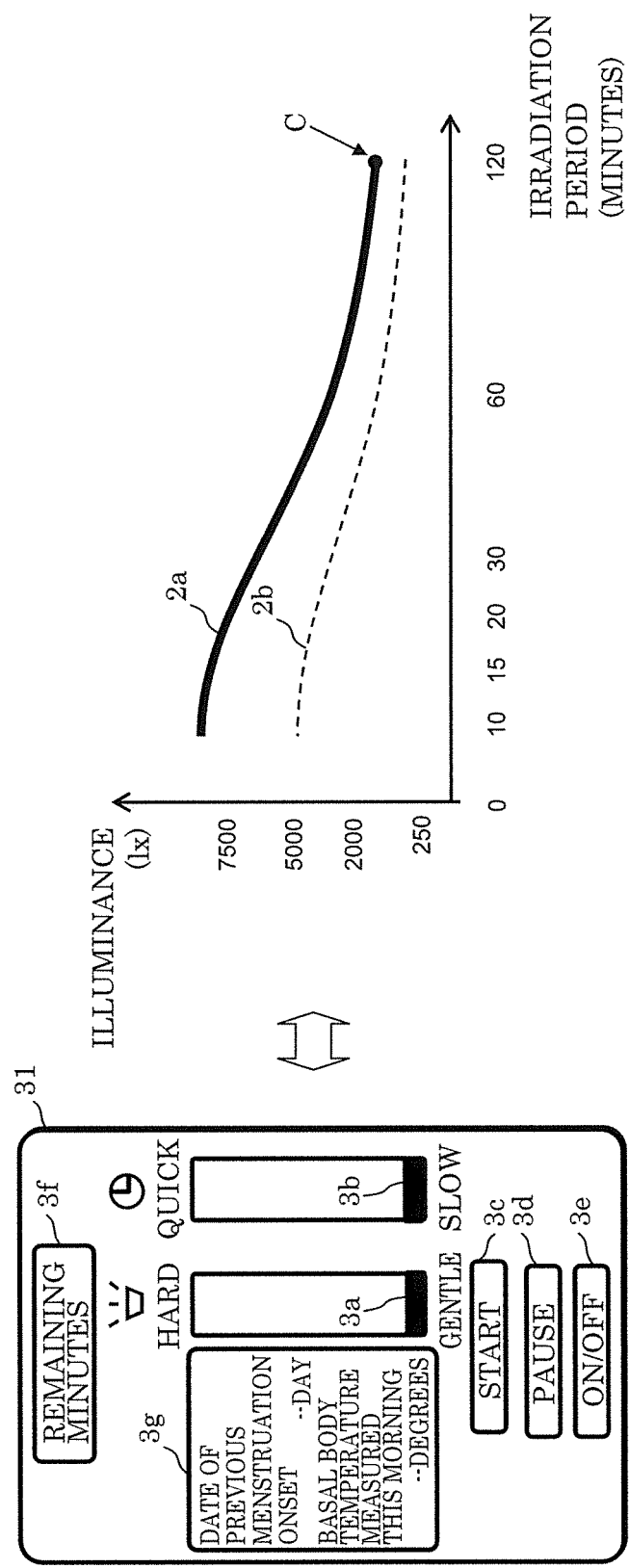
FIG. 8 is an explanatory diagram illustrating a display example of a UI and characteristic information according to Embodiment 2.

FIG. 8 is an explanatory diagram illustrating a display example of UI 3 and characteristic information according to Embodiment 2. The display example on the left side in FIG. 8 differs from FIG. 2 in that display item 3g is added. The following description focuses on the differences.

Display item 3g is an input box for manually inputting menstruation-related information 21b by a user. In the display example illustrated in the diagram, "date of previous menstruation onset" and "basal body temperature measured this morning" are illustrated as examples of part of input items. Menstruation-related information 21b may be manually inputted by a user using UI 3, or may be inputted to lighting system 1 via an application of a smartphone, etc. In addition, menstruation-related information 21b may be selected in advance from a plurality of expression items capable of subjectively expressing the severity of symptoms (feeling tired, a mild symptom of PMS, requesting hard optical treatment, etc.), or may be a specific numerical value information items (the number of days elapsed from the previous menstruation onset, a basal body temperature measured this morning, a heart rate, etc.)

When a user inputs menstruation-related information 21b to display item 3g, or when menstruation-related information 21b indicating the current conditions of the user is stored in storage 21, controller 2 determines the severity of symptoms of premenstrual syndrome, and selects one characteristic curve data item corresponding to the determined severity, from among a plurality of characteristic curve data items. In the characteristic information on the right side in FIG. 8, the characteristic curve indicated by a solid line corresponds to characteristic curve data item 2a, and the characteristic curve indicated by a dashed line corresponds to characteristic curve data item 2b. Furthermore, on the right side in FIG. 8, it is indicated that characteristic curve data item 2a is selected from among a plurality of characteristic curve data items, on the basis of the menstruation-related information inputted to display item 3g. The positions of the slider icons of display items 3a and 3b on the left side in FIG. 8 correspond to point C (120 minutes, approximately 1000 lx) on characteristic curve data item 2a on the right side in FIG. 8. The user is allowed to easily specify, as the user wishes, one of the amount of light and the irradiation period while viewing display items 3a and 3b, after the input operation to display item 3g has been completed.

[2.3 An Operation Example of Controller 2]

Next, an operation example of lighting system 1 controlled by controller 2 shall be described.

Controller 2 according to Embodiment 2 differs from Embodiment 1 in performing selecting of a characteristic curve. The following description focuses on the differences.

Figure 9:
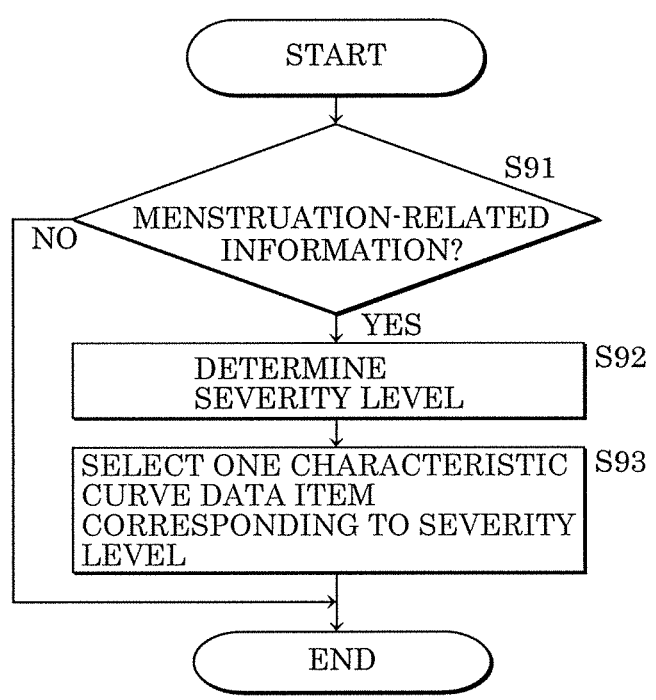
FIG. 9 is a flowchart illustrating an example of a process of selecting a characteristic curve according to Embodiment 2.

FIG. 9 is a flowchart illustrating an example of a process of selecting a characteristic curve according to Embodiment 2. The process of selecting described in the diagram is executed according to a user operation performed on display item 3g. The user should perform the user operation performed on display item 3g prior to the user operation performed on display item 3a or 3b.

As, illustrated in FIG. 9, controller 2 determines whether or not inputting of menstruation-related information to display item 3g using UI 3 is completed (S91). When the inputting is completed, controller determines the severity (severity level) of premenstrual syndrome on the basis of the menstruation-related information (S92), and selects one characteristic curve data item corresponding to the determined severity level from among a plurality of characteristic curve data items 2a, 2b, . . . stored in storage 21 (S93). On the right side in FIG. 8, it is indicated that characteristic curve data item 2a is selected.

It should be noted that, in Step S91, instead of determining whether or not the user's inputting operation to display item 3g is completed, controller 2 may determine whether or not the user's current menstruation-related information 21b is stored in storage 21 from an SD card, a USB memory, or cloud (a server on the Internet).

As described above, according to Embodiment 2, storage 21 stores, as the characteristic information, a plurality of characteristic curve data items having mutually different negative correlations, and controller 2 selects one of the plurality of characteristic curve data items according to the severity (i.e., severity level) of premenstrual syndrome of a user. In this manner, lighting system 1 is capable of determining an optimal amount of light and an optimal irradiation period according to the severity (i.e., severity level) of premenstrual syndrome of the user.

[2.3 An Example of Menstruation-Related Information]

Next, menstruation-related information shall be described.

FIG. 10 is an explanatory diagram illustrating an example of menstruation-related information according to Embodiment 2. FIG. 10 illustrates items (the number of days of menstrual cycle, etc.) and data (d1, etc.) included in menstruation related information. Storage 21 stores, as menstruation-related information 21b, data items corresponding to the items illustrated in the diagram. Menstruation-related information 21b includes at least one of the items illustrated in the diagram. More specifically, menstruation-related information 21b includes at least one of: the number of days of a menstrual cycle; the date menstruation onset; a menstrual cycle; a basal body temperature; an amount of luteinizing hormone secretion; an amount of luteohormone secretion; an amount of estrogenic hormone secretion; a subjective level of menstrual pain (not at all, mild, moderate, severe); the premenstrual symptoms screening tool (PPST) which is subjective estimation of premenstrual syndrome; and a premenstrual symptoms questionnaire (PSQ). Controller 2 determines, in Step S92 is FIG. 9, the severity level (for example, not at all, mild, moderate, severe, premenstrual dysphoric disorder (PMDD)) of premenstrual syndrome, which is calculated from each of the items illustrated in FIG. 10. Here, the PMDD is a segment indicating a symptom severer than "severe" of the premenstrual syndrome.

Here, the above-described PSST shall be described.

FIG. 11A is a diagram illustrating an example of data items related to mental and physical symptoms of the PSST illustrated in FIG. 10. This example of data items include data items indicating to which of four levels a to d each of items 1 to 13 and 14-1 to 14-5 related to the mental and physical symptoms of the PSST corresponds.

Figure 11B:
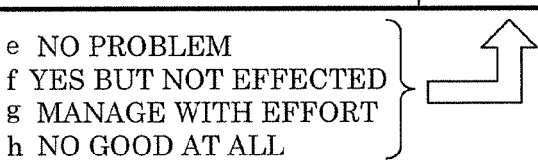
FIG. 11B is an explanatory diagram illustrating an example of data items related to social symptoms of the PSST illustrated in FIG. 10.

FIG. 11B is a diagram illustrating an example of data items related to social symptoms of the PSST illustrated in FIG. 10. This example of data items include data items indicating to which of four levels e to h each of the items A to E related to the social symptoms of the PSST corresponds.

Here, the above-described PSQ shall be described.

FIG. 12 is an explanatory diagram illustrating an example of data items related to the PSQ illustrated in FIG. 10. This example of data items include data items indicating to which of four levels i to l each of items 1 to 11 of (A) and 1 to 3 of (B) of the PSQ corresponds.

Here, the menstrual cycle and symptoms on which the above-described PSST and PSQ are based shall be briefly described with reference to FIG. 13 and FIG. 14.

FIG. 13 is a diagram illustrating mental, physical, and skin conditions according to a menstrual cycle. In this diagram, a relationship between the number of days of menstruation onset, a phase, a period of developing PMS, a mental state, a physical state, and skin conditions is indicated. In general, the physical and mental states change during four phases of the menstrual cycle, as illustrated in FIG. 13. In a period from the latter half of the luteal phase to three or four days after the menstruation onset, symptoms of premenstrual syndrome (PMS) occur as illustrated in the table.

Figure 14:
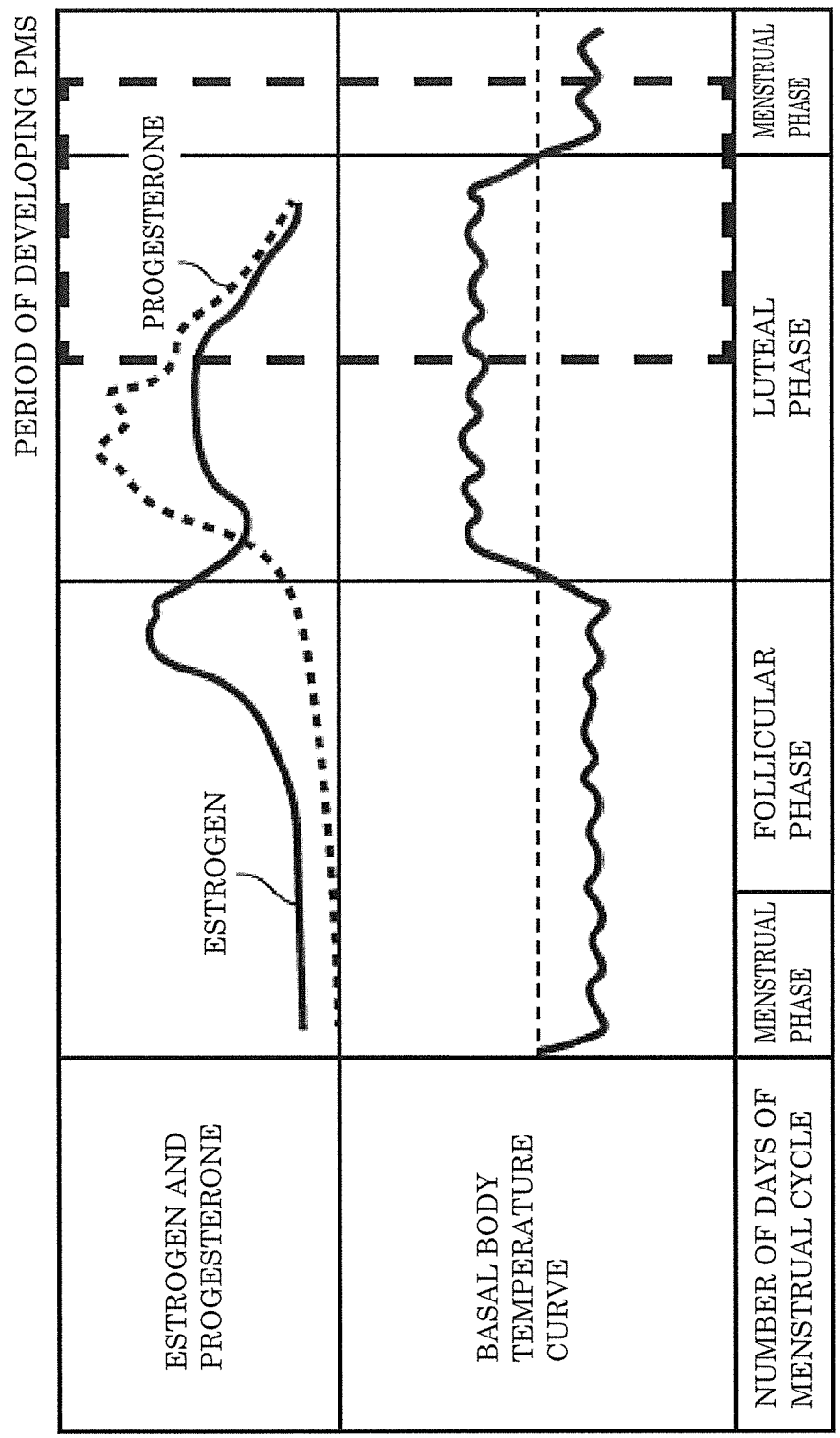
FIG. 14 is a diagram illustrating hormone secretion and basal body temperatures according to a menstrual cycle.

FIG. 14 is a diagram illustrating hormone secretion and basal body temperatures according to a menstrual cycle. In this diagram, the secretion of each of estrogen (ovulation hormone) and progesterone (luteohormone), and a basal body temperature curve, according to the menstrual cycle are illustrated. The main cause of PMS is considered to be decrease in serotonin due to decrease in luteohormone (progesterone), and a mentally unstable state, drowsiness, sleeplessness, headache, etc., are likely to be caused. In FIG. 14, a frame enclosed by a dashed line indicates a period of onset of PMS. The symptoms of PMS start to develop approximately one week before the menstruation onset, the symptoms peak several days before the menstruation onset, and the symptoms decrease and disappear with the menstruation onset. The menstrual pain appears, in general, with the menstruation onset, peaks on the second day of menstruation, and the symptom decreases and disappears on and after the third day of menstruation.

With respect to the above-described PMS, one characteristic curve data item is selected according to the severity of PMS from among a plurality of characteristic curve data items in Embodiment 2. In this manner, lighting system 1 is capable of determining a suitable amount of light and a suitable irradiation period according to the symptoms of PMS.

[2.4 Modification Examples]

Next, a configuration of a lighting system according to modification examples of Embodiment 2 shall be described. The modification examples differ from the embodiments mainly in that storage 21 stores sleep-related information instead of the menstruation-related information. The following description focuses on the differences.

Figure 15:
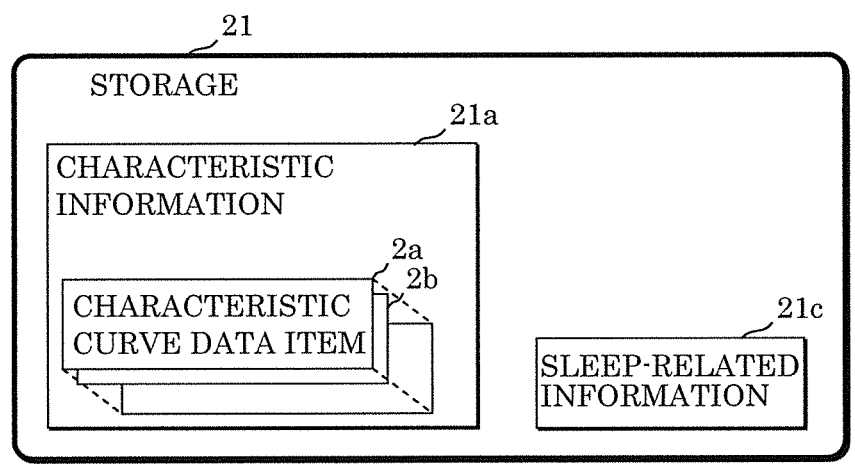
FIG. 15 is an explanatory diagram illustrating an example of characteristic information and sleep-related information which are stored in a storage according to a modification example of Embodiment 2.

FIG. 15 is an explanatory diagram illustrating an example of characteristic information 21a and sleep-related information 21c which are stored in storage 21 according to the modification example of Embodiment 2.

Storage 21 stores characteristic information 21a and sleep-related information 21c. Sleep-related information 21c indicates, for example, severity of a sleep disorder or a satisfaction level of sleep of a user, and is a reference for selecting one of the plurality of characteristic curve data items.

[2.5 A Display Example of the User Interface]

Next, a display example of user interface 3 which receives a user operation according to the present modification example shall be described.

Figure 16:
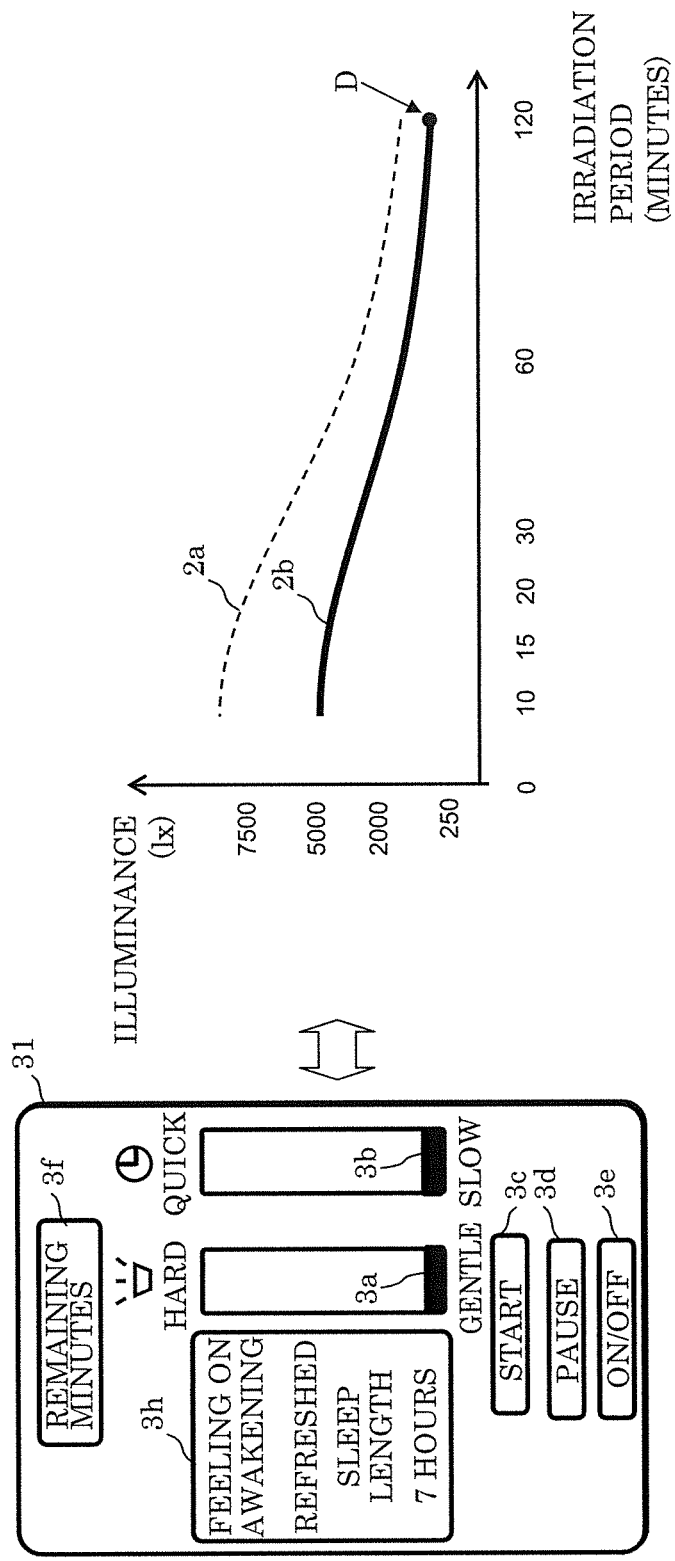
FIG. 16 is an explanatory diagram illustrating a display example of a UI and characteristic information according to the modification example of Embodiment 2.

FIG. 16 is an explanatory diagram illustrating a display example of UI 3 and characteristic information according to the modification example of Embodiment 2. The display example on the left side in FIG. 16 differs from FIG. 2 in that display item 3h is added. The following description focuses on the differences.

Display item 3h is an input box for manually inputting sleep-related information 21c by a user. In the display example illustrated in the diagram, "feeling on awakening" and "sleep length" are illustrated as examples of part of input items. Sleep-related information 21c may be manually inputted by a user using storage 21 or UI 3, or may be inputted to lighting system 1 via an application of a smartphone, etc. In addition, sleep-related information 21c may be selected in advance from a plurality of expression items capable of subjectively expressing the severity of a sleep disorder or the satisfaction level of sleep, or may be a specific numerical value information items.

When a user inputs sleep-related information 21c to display item 3h, or when sleep-related information 21c indicating the current state of the user is stored in storage 21, controller 2 determines the severity of a sleep disorder or the satisfaction level of sleep, and selects one characteristic curve data item correspond to the determined severity from among a plurality of characteristic curve data items. In the characteristic information on the right side in FIG. 16, the characteristic curve indicated by a solid line corresponds to characteristic curve data item 2b, and the characteristic curve indicated by a dashed line corresponds to characteristic curve data item 2a. Furthermore, on the right side in FIG. 16, it is indicated that characteristic curve data item 2b is selected from among a plurality of characteristic curve data items, on the basis of the sleep-related information inputted to display item 3h. The positions of the slider icons of display items 3a and 3b on the left side in FIG. 16 correspond to point D (120 minutes, approximately 500 lx) on characteristic curve data item 2b on the right side in FIG. 16. The user is allowed to easily specify, as the user wishes, one of the amount of light and the irradiation period while viewing display items 3a and 3b, after the input operation to display item 3h is completed.

[2.6 An Operation Example of Controller 2]

Next, an operation example of lighting system 1 controlled by controller 2 shall be described.

Controller 2 according to the present modification differs from Embodiment 1 in performing selecting of a characteristic curve. The following description focuses on the differences.

Figure 17:
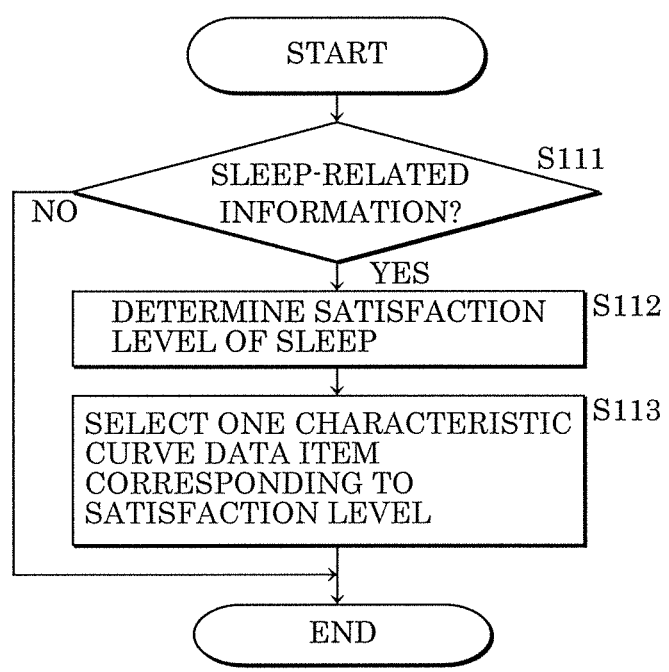
FIG. 17 is a flowchart illustrating an example of a process of selecting a characteristic curve according to the modification example of Embodiment 2.

FIG. 17 is a flowchart illustrating an example of a process of selecting a characteristic curve according to the modification example of Embodiment 2. The process of selecting described in the diagram is executed according to a user operation performed on display item 3h. The user should perform the user operation performed on display item 3h prior to the user operation performed on display item 3a or 3b.

As illustrated in FIG. 17, controller 2 determines whether or not inputting of sleep-related information to display item 3h using UI 3 is completed (S111). When the inputting is completed, controller 2 determines the severity (severity level) of the sleep disorder or the satisfaction level of sleep on the basis of the sleep-related information (S112), and select one characteristic curve data item corresponding to the determined severity level from among a plurality of characteristic curve data items 2a, 2b, . . . stored in storage 21 (S113). On the right side in FIG. 16, it is indicated that characteristic curve data item 2b is selected.

It should be noted that, in Step S111, instead of determining whether or not the user's inputting operation to display item 3h is completed, controller 2 may determine whether or not the user's current sleep-related information 21c is stored in storage 21 from an SD card, a USB memory, or cloud (a server on the Internet).

As described above, according o Embodiment 2, storage 21 stores, as the characteristic information, a plurality of characteristic curve data items having mutually different negative correlations between, and controller 2 selects one of the plurality of characteristic curve data items according to the severity (i.e., severity level) of the sleep disorder or the satisfaction level of sleep of a user. In this manner, lighting system 1 is capable of determining an optimal amount of light and an optimal irradiation period according to the severity (i.e., severity level) of the sleep disorder or the satisfaction level of sleep of a user.

[2.7 An Example of Sleep-Related Information]

Next, sleep-related information shall be described.

FIG. 18 is an explanatory diagram illustrating an example of data items of sleep-related information according to the modification example of Embodiment 2. FIG. 18 illustrates items (sleep length of the previous day, etc.) and data (d21, etc.) included in sleep-related information. Storage 21 stores, as sleep-related information 21c, data corresponding to the items illustrated in the diagram. Sleep-related information 21c includes, for example, at least one of the items illustrated in the diagram. More specifically, sleep-related information 21c includes at least one of: a sleep length of the previous day; the time of sleep; awaking time of the day; sleep length of several days; amount of activity; a subjective estimation of sleep quality; a subjective satisfaction level of sleep; a respiratory condition; brain wave; and body motion. Controller 2 determines the severity of a sleep disorder or the satisfaction level of sleep calculated on the basis of each item illustrated in FIG. 18, in Step S112 of FIG. 17.

Here, "a subjective estimation of sleep quality" which is included in the sleep-related information shall be described.

FIG. 19 is an explanatory diagram illustrating an example of data items of part of sleep-related information according to the modification example of Embodiment 2. Data indicating "a subjective estimation of sleep quality" in the diagram includes data indicating to which one of a to d each item of 1 to 16 corresponds.

According to the modification example of Embodiment 2, one characteristic curve data item is selected, from among a plurality of characteristic curve data items, according to the severity of the severity of a sleep disorder or the satisfaction level of sleep, using the above-described sleep-related information. In this manner, lighting system 1 is capable of determining a suitable amount of light and a suitable irradiation period according to the severity of the severity of a sleep disorder or the satisfaction level of sleep.

(Embodiment 3)

Lighting system 1 according to Embodiment 3 differs from Embodiment 1 and Embodiment 2, in that a user can specify an amount of blue light in addition to the operations of Embodiment 1 and Embodiment 2.

[3.1 A Configuration Example of a Lighting System]

The overall configuration of lighting system 1 according to Embodiment 3 is substantially the same as the overall configuration of lighting system 1 according to Embodiment 1. The following description focuses on the differences.

Figure 20:
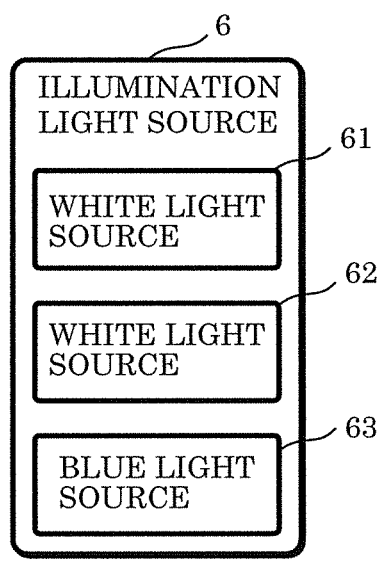
FIG. 20 is an explanatory diagram illustrating a configuration example of an illumination light source according to Embodiment 3.

FIG. 20 is an explanatory diagram illustrating a configuration example of illumination light source 6 according to Embodiment 3. Illumination light source 6 includes white light source 61, white light source 62, and blue light source 63.

For example, white light source 61 has a color temperature higher than a color temperature of white light source 62.

Blue light source 63 has a spectrum having a peak wavelength within 40 nm of 480 nm.

The following is the reason why a user is allowed to specify the amount of blue light in Embodiment 3.

In optical treatment, high-illuminance radiation of light is performed at the time of awaking or during daytime, to treat disturbance of circadian rhythm, drowsiness, and sleeplessness, due to seasonal depression, delayed sleep phase syndrome, and premenstrual syndrome to adjust the secretion rhythm of melatonin and the circadian rhythm. The peak (action spectrum) of a wavelength of light that affects the secretion of melatonin is considered to be approximately 480 nm, and blue light including the wavelength of approximately 480 nm is regarded as being effective for the treatment.

According to the present embodiment, it is possible to control the amount of blue light to be emitted so as to increase the amount when the symptom is severe and decrease the amount when the symptom is mild.

It is possible to adjust the biological rhythm and decrease the severity level of symptoms of premenstrual syndrome, by applying irradiation before the symptoms develop. The symptoms decrease without irradiation when the menstruation ends, and thus it is possible to control the amount of blue light so as to decrease, after the menstruation onset, the amount of blue light used for irradiation to be smaller than the amount of blue light emitted at the time of menstruation onset.

In addition, since the severity level of the symptoms of premenstrual syndrome and menstrual pain changes according to the number of days of a menstrual cycle, it is also possible to estimate the severity level of the symptoms on the basis of the number of days of a menstrual cycle, the date of menstruation onset, and the menstrual cycle, to control the amount of blue light.

It is also possible to estimate the severity level of the symptoms on the basis of a value of each of the basal body temperature, the luteinizing hormone secretion, the luteohormone secretion, and the estrogenic hormone secretion, to control the amount of blue light.

For the reasons describe above, it is possible to increase the advantageous effects of radiation of light, by allowing the amount of blue light to be specified.

[3.2 A Display Example of the User Interface]

Next, a display example of user interface 3 which receives a user operation shall be described.

Figure 21:
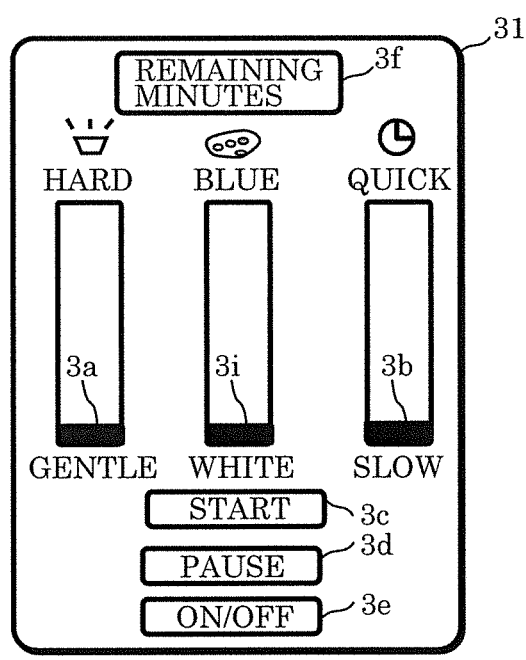
FIG. 21 is a diagram illustrating a display example of a UI according to Embodiment 3.

FIG. 21 is a diagram illustrating a display example of UI 3 according to Embodiment 3. The display example in FIG. 21 differs from FIG. 2 in that display item 3$i$ is added. The following description focuses on the differences.

Display item 3$i$ is an operation icon for specifying a color component by a user, and indicated by a slider icon which can specify the color temperature of illumination light source 6 within a range from whitish illumination light to bluish illumination light.

[3.3 Usability of Blue Light]

Next, the emission spectrum of illumination light source 6, in particular the usability of blue light, shall be described.

Figure 22:
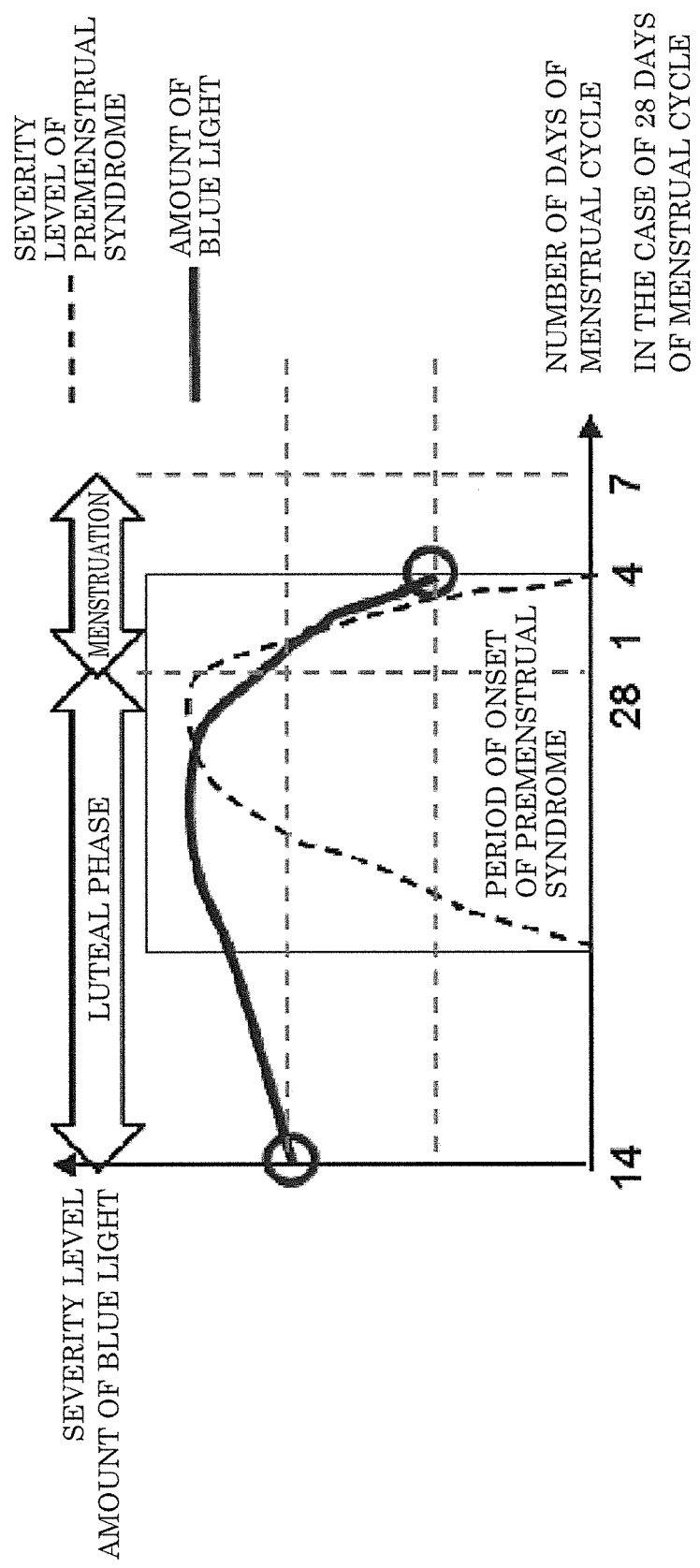
FIG. 22 is a diagram illustrating a suitable amount of blue light and the severity level according to the menstrual cycle according to Embodiment 3.

FIG. 22 is a diagram illustrating a suitable amount of blue light and the severity level according to the menstrual cycle according to Embodiment 3.

As illustrated in FIG. 22, radiation of blue light is utilized starting from the anterior half of the luteal phase that is the phase before the symptoms of premenstrual syndrome start to develop, that is, approximately two weeks before the menstruation onset, and the radiation of blue light can be ended on the fourth day of the menstruation when the symptoms decrease and disappear.

In this manner, it is possible to obtain the effect of alleviating the symptoms before the premenstrual syndrome starts to develop.

[3.4 Other Display Examples of the User Interface]

Figure 23:
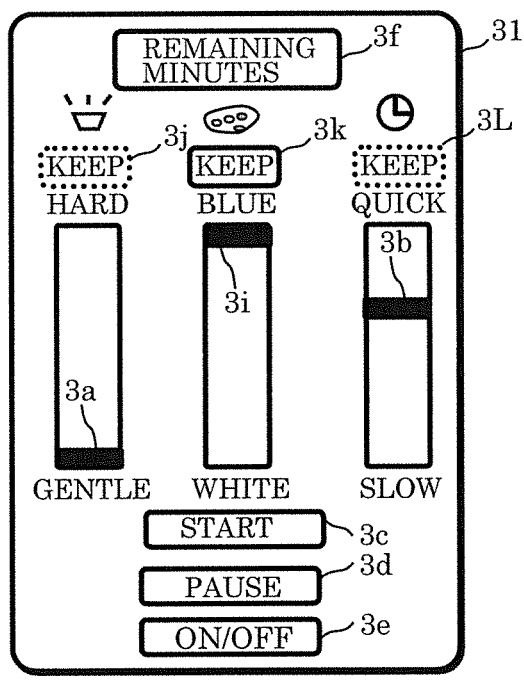
FIG. 23 is a diagram illustrating another display example of the UI according to Embodiment 3.

FIG. 23 is a diagram illustrating another display example of UI 3 according to Embodiment 3 FIG. 23 differs from FIG. 21 in that display items 3$j$, 3$k$, 3L are added. The following description focuses on the differences.

Display items 3$j$, 3$k$, 3L are operation icons corresponding one to one to a plurality of parameters including the amount of light and the irradiation period, and operation keep button icons for specifying whether to keep or not to keep the values of the plurality of parameters. To keep refers to not permitting a user operation on the parameter and not to keep refers to permitting a user operation on the parameter. Display item 3$k$ indicated by a solid line frame illustrated in FIG. 23 indicates "to keep", and display items 3$j$ and 3L indicated by dashed line frames indicate "not to keep".

The slider of display item 3$i$ illustrated in FIG. 23 is located at a position closest to the "blue" side. In this state, the slider of display item 3$i$ is set to "keep" by display item 3$k$. In other words, in the display example illustrated in FIG. 23, radiation of the maximum blue light is specified and kept.

Figure 24A:
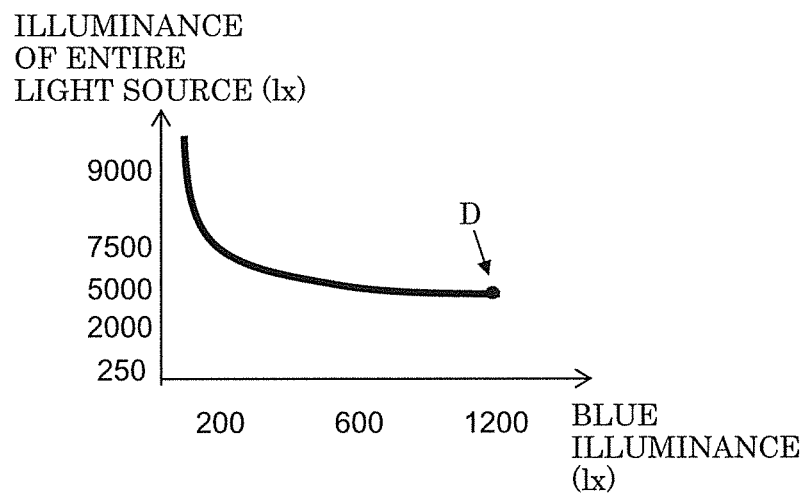
FIG. 24A is a diagram illustrating an example of characteristic information indicating blue illuminance and illuminance of the entire light source according to Embodiment 3.

FIG. 24A is a diagram illustrating an example of characteristic information (also referred to as dimming curve data) indicating blue illuminance and illuminance of the entire light source according to Embodiment 3. For example, the horizontal axis indicates the illuminance of blue light source 63 and the vertical axis indicates the illuminance, of the entire light source. The position of the curve illustrated in FIG. 24A corresponds to the position of the slider of display item 3$i$ illustrated in FIG. 23. The slider of display item 3$i$ illustrated in FIG. 23 is located at the position closest to the "blue" side. This position corresponds to point D illustrated in. FIG. 24A.

Figure 24B:
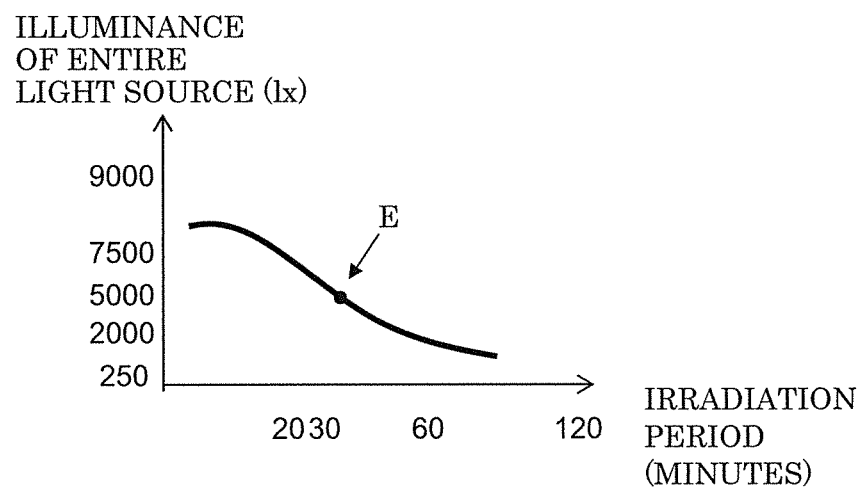
FIG. 24B is a diagram illustrating an example of characteristic information indicating the amount of light and the irradiation period according to Embodiment 3.

FIG. 24B is a diagram illustrating an example of characteristic information indicating the amount of light and the irradiation period according to Embodiment 3. FIG. 24B is similar to FIG. 2. The sliding positions of display items 3$a$, 3$i$, and 3$b$ illustrated in FIG. 23 correspond to point E illustrated in FIG. 24B.

With the above-described display example, it is possible for a user to easily specify the amount of blue light, leading to increase in the advantageous effect of radiation of light (alleviation of the symptoms).

Figure 25:
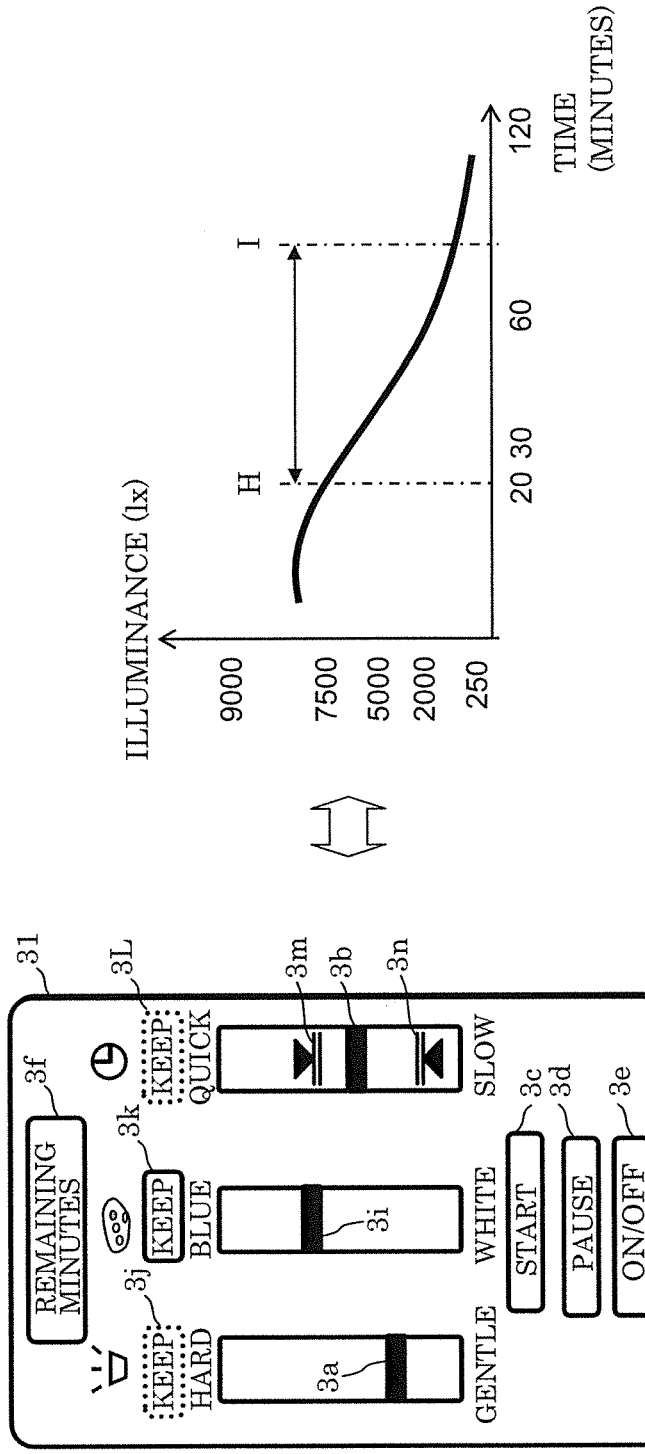
FIG. 25 is an explanatory diagram illustrating yet another display example of the UI and characteristic information according to Embodiment 3.

FIG. 25 is an explanatory diagram illustrating yet another display example of UI 3 and characteristic information according to Embodiment 3. FIG. 25 differs from FIG. 23 in that display items 3$m$ and 3$n$ are added. The following description focuses on the differences.

Display item 3$m$ is a mark indicating an upper limit or a lower limit of the range that can be specified in the entire slide range of display item 3$b$.

Display item 3$n$ is a mark indicating upper limit or a lower limit of the range that can be specified in the entire slide range of display item 3$b$.

With this display example, it is possible to allow a user to visually observe the range that can be specified, leading to further facilitating the user operation.

As described above, the lighting system according to each of the embodiments includes: illumination light source 6 which irradiates a user with illumination light; user interface 3 which receives a user operation; controller 2 which controls an amount of light of illumination light source 6 and an irradiation period of illumination light source 6; and storage 21 which stores characteristic information having a negative correlation between the amount of light of illumination light source 6 and the irradiation period, wherein when user interface 3 receives a user operation which specifies a value of one of the amount of light of illumination light source 6 and the irradiation period, controller 2 determines a value of the other of the amount of light of illumination light source 6 and the irradiation period according to the characteristic information and controls illumination light source 6 according to the value of the one of the amount of light of illumination light source 6 and the irradiation period which has been specified and the value of the other of the amount of light of illumination light source 6 and the irradiation period which has been determined.

With this, it is possible for a user to specify with no inhibition desired one of parameters (one of the amount of light and the irradiation period) without the need to consider a suitable combination of the amount of light and the irradiation period in optical treatment. In other words, a user can obtain a suitable combination of the amount of light and the irradiation period in lighting system 1, by specifying a request regarding the amount of light or the irradiation period (for example, hoping to be exposed to weak light or strong light, hoping to shorten the irradiation period or lengthen the irradiation period). Here, controller 2 may receive, via user interface 3, at least one of menstruation-related information and sleep-related information of the user; select gone of the plurality of characteristic curve data items based on the at least one of the menstruation-related information and the sleep-related information of the user; and determine the value of the other of the amount of light of illumination light source 6 and the irradiation period according to the one of the plurality of characteristic curve data items which has been selected. Here, controller 2 may receive, via an application of a smartphone, at least one of menstruation-related information and sleep-related information of the user; select one of the plurality of characteristic curve data items based on the at least one of the menstruation-related information and the sleep-related information of the user; and determine the value of the other of the amount of light of illumination light source 6 and the irradiation period according to the one of the plurality of characteristic curve data items which has been selected.

Here, the characteristic information may include a plurality of characteristic curve data items 2a and 2b having mutually different negative correlations between the amount of light of the illumination light source and the irradiation period, and the controller may select one of the plurality of characteristic curve data items on the basis of at least one of menstruation-related information 21b and sleep-related information 21c of the user, and determine the value of the other of the amount of light of the illumination light source and the irradiation period according to the one of the plurality of characteristic curve data items which has been selected.

Here, the plurality of characteristic curve data items may each correspond to severity of a symptom of premenstrual syndrome or a sleep disorder.

Here, controller may 2 further determine a severity of the premenstrual symptoms from the menstruation-related information or a severity of the sleep disorder, and selects one of the plurality of characteristic curve data items based on the severity.

Here, the illumination light source may include a white light source which emits white light and a blue light source which emits blue light.

Here, the storage may further store dimming curve data in which the amount of light of the illumination light source and an amount of light of the blue light source are associated with each other, and the controller may determine the amount of light of the blue light source according to the dimming curve data.

Here, the user interface may include: a display panel which displays a display item indicating a value of the amount of light of the illumination light source and a value of the irradiation period; and an operating portion which receives a user operation, and the controller may update the display item to display the value of the one of the amount of light of the illumination light source and the irradiation period which has been specified and the other of the amount of light of the illumination light source and the irradiation period which has been determined.

With this, a user can easily specify a desired parameter while visually observing display items of parameters (here, the amount of light or the irradiation period).

Here, the display panel may display remaining time of the irradiation period after starting radiation of the illumination light.

Here, the display panel may display a mark which indicates at least one of an upper limit and a lower limit of a range that can be specified for one of the amount of light of the illumination light source and the irradiation period.

Here, the display panel may display a plurality of operation images corresponding one to one to a plurality of parameters including the amount of light of the illumination light source and the irradiation period, and a plurality of operation button images each indicating whether or not to keep a value of a corresponding one of the plurality of parameters, and the operating portion may receive a user operation to the plurality of operation images and the plurality of operation button images which are displayed on the display panel.

The operation device according to Embodiment 1 is operation device 4 which controls illumination light source 6 that irradiates a user with illumination light. Operation device 4 includes: user interface 3 which receives a user operation; controller 2 which controls an amount of light of illumination light source 6 and an irradiation period of illumination light source 6; and storage 21 which stores characteristic information having a negative correlation between the amount of light of illumination light source 6 and the irradiation period. When user interface 3 receives an operation which specifies a value of one of the amount of light of illumination light source 6 and the irradiation period, controller 2 determines a value of the other of the amount of light of illumination light source 6 and the irradiation period according to the characteristic information and controls illumination light source 6 according to the value of the one of the amount of light of illumination light source 6 and the irradiation period which has been specified and the value of the other of the amount of light of illumination light source 6 and the irradiation period which has been determined.

The light irradiation method according to Embodiment 1 is a light irradiation method for irradiating a user with illumination light. The light irradiation method includes: receiving a user operation which specifies a value of one of an amount of light and an irradiation determining a value of the other of the amount of light and the irradiation period which is not specified, according to characteristic information having a negative correlation between the amount of light and the irradiation period; and irradiating the user with the illumination light according to the value of the one of the amount of light and the irradiation period which has been specified and the value of the other of the amount of light and the irradiation period which has been determined.

With this, it is possible for a user to specify with no inhibition desired one of parameters (one of the amount of light and the irradiation period) without the need to consider a suitable combination of the amount of light and the irradiation period in optical treatment.

Although the lighting system, the operation device, and the irradiation method according to the present disclosure have been described based on the above-described embodiments, the present disclosure is not, limited to the above-described embodiments. Other forms in which various modifications apparent to those skilled in the art are applied to the present embodiment or forms in which some structural components according to the embodiments and modification examples are arbitrarily combined within the scope of the present disclosure are also included within the scope of the present disclosure unless such changes and modifications depart from the scope of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A lighting system, comprising:
an illumination light source which irradiates a user with illumination light;
a user interface which receives a user operation;
a controller which controls an amount of light of the illumination light source and an irradiation period of the illumination light source; and
a storage which stores characteristic information having a negative correlation between the amount of light of the illumination light source and the irradiation period, wherein:
when the user interface receives a user operation which specifies a value of one of the amount of light of the illumination light source and the irradiation period, the controller determines a value of an other of the amount of light of the illumination light source and the irradiation period according to the characteristic information and controls the illumination light source according to the value of the one of the amount of light of the illumination light source and the irradiation period which has been specified and the value of the other of the amount of light of the illumination light source and the irradiation period which has been determined,
the characteristic information includes a plurality of characteristic curve data items having mutually different negative correlations between the amount of light of the illumination light source and the irradiation period,
the controller selects one of the plurality of characteristic curve data items on the basis of at least one of menstruation-related information and sleep-related information of the user, and determines the value of the other of the amount of light of the illumination light source and the irradiation period according to the one of the plurality of characteristic curve data items which has been selected, and
the plurality of characteristic curve data items each correspond to severity of a symptom of premenstrual syndrome or a sleep disorder.

2. The lighting system according to claim 1, wherein the illumination light source includes a white light source which emits white light and a blue light source which emits blue light.

3. The lighting system according to claim 2, wherein the storage further stores dimming curve data in which the amount of light of the illumination light source and an amount of light of the blue light source are associated with each other, and
the controller determines the amount of light of the blue light source according to the dimming curve data.

4. The lighting system according to claim 1, wherein:
the user interface includes:
a display panel which displays a display item indicating a value of the amount of light of the illumination light source and a value of the irradiation period; and
an operating portion which receives a user operation, and
the controller updates the display item to display the value of the one of the amount of light of the illumination light source and the irradiation period which has been specified and the other of the amount of light of the illumination light source and the irradiation period which has been determined.

5. The lighting system according to claim 4, wherein the display panel displays remaining time of the irradiation period after starting radiation of the illumination light.

6. The lighting system according to claim 4, wherein the display panel displays a mark which indicates at least one of an upper limit and a lower limit of a range that can be specified for one of the amount of light of the illumination light source and the irradiation period.

7. The lighting system according to claim 4, wherein the display panel displays a plurality of operation images corresponding one to one to a plurality of parameters including the amount of light of the illumination light source and the irradiation period, and a plurality of operation button images each indicating whether or not to keep a value of a corresponding one of the plurality of parameters, and
the operating portion receives a user operation to the plurality of operation images and the plurality of operation button images which are displayed on the display panel.

8. An operation device which controls an illumination light source that irradiates a user with illumination light, the operation device comprising:
a user interface which receives a user operation;
a controller which controls an amount of light of the illumination light source and an irradiation period of the illumination light source; and
a storage which stores characteristic information having a negative correlation between the amount of light of the illumination light source and the irradiation period, wherein:
when the user interface receives an operation which specifies a value of one of the amount of light of the illumination light source and the irradiation period, the controller determines a value of an other of the amount of light of the illumination light source and the irradiation period according to the characteristic information and controls the illumination light source according to the value of the one of the amount of light of the illumination light source and the irradiation period which has been specified and the value of the other of the amount of light of the illumination light source and the irradiation period which has been determined
the characteristic information includes a plurality of characteristic curve data items having mutually different negative correlations between the amount of light of the illumination light source and the irradiation period,
the controller selects one of the plurality of characteristic curve data items on the basis of at least one of menstruation-related information and sleep-related information of the user, and determines the value of the other of the amount of light of the illumination light source and the irradiation period according to the one of the plurality of characteristic curve data items which has been selected, and the plurality of characteristic curve data items each correspond to severity of a symptom of premenstrual syndrome or a sleep disorder.

9. A light irradiation method for irradiating a user with illumination light, the light irradiation method comprising:
receiving a user operation which specifies a value of one of an amount of light and an irradiation period;
determining a value of an other of the amount of light and the irradiation period which is not specified, according to characteristic information having a negative correlation between the amount of light and the irradiation period, the characteristic information including a plurality of characteristic curve data items having mutually different negative correlations between the amount of light and the irradiation period;
irradiating the user with the illumination light according to the value of the one of the amount of light and the irradiation period which has been specified and the value of the other of the amount of light and the irradiation period which has been determined;
selecting one of the plurality of characteristic curve data items on the basis of at least one of menstruation-related information and sleep-related information of the user; and
determining the value of the other of the amount of light and the irradiation period according to the one of the plurality of characteristic curve data items which has been selected,
wherein the plurality of characteristic curve data items each correspond to severity of a symptom of premenstrual syndrome or a sleep disorder.

* * * * *